United States Patent [19]

Gude et al.

[11] Patent Number: 4,496,710

[45] Date of Patent: Jan. 29, 1985

[54] PROCESS FOR THE PRODUCTION OF FLAT VARNISHES

[75] Inventors: Fritz Gude, Herne; Herbert Haferkorn; Heinz Riemer, both of Bottrop; Günter Dörmann, Bochum, all of Fed. Rep. of Germany

[73] Assignee: Chemische Werke Huls Aktiengesellschaft, Marl, Fed. Rep. of Germany

[21] Appl. No.: 583,229

[22] Filed: Feb. 24, 1984

[30] Foreign Application Priority Data

Mar. 29, 1983 [DE] Fed. Rep. of Germany ....... 3311404

[51] Int. Cl.$^3$ .............................................. C08G 59/42
[52] U.S. Cl. .................... 528/114; 528/350; 548/347
[58] Field of Search ................ 548/347; 528/114, 350

[56] References Cited

U.S. PATENT DOCUMENTS

| | | | |
|---|---|---|---|
| 3,356,645 | 12/1967 | Warren | 528/114 X |
| 3,746,686 | 7/1973 | Marshall et al. | 528/114 |
| 3,947,384 | 3/1976 | Schulde et al. | 528/114 |

*Primary Examiner*—Earl A. Nielsen
*Attorney, Agent, or Firm*—Oblon, Fisher, Spivak, McClelland & Maier

[57] ABSTRACT

The object of the invention is a process for the production of flat varnishes based on powder coatings of 1,2-epoxy compounds with at least one 1,2-epoxy group in the molecule and a lower melting point of >40° C., salts of aromatic carboxylic acids with 3 and more carboxyl groups and imidazolines as curing agents, as well as the usual additives and the application of the powdered varnish upon the objects to be varnished and heating of these objects to temperatures of 160°–240° C., whereby the salt of 2-phenyl-methyl-Δ2-imidazoline and trimellitic acid is substituted up to 60 mole % by a salt of 2-phenyl-Δ2-imidazoline and trimellitic acid.

9 Claims, No Drawings

PROCESS FOR THE PRODUCTION OF FLAT VARNISHES

BACKGROUND OF THE INVENTION

1. Field of the Invention

The production of salts from polycarboxylic acids with three and more carboxyl groups and cyclic amidines in organic solvents for the purpose of hardening epoxy resins to flat coatings is described in DE-AS No. 23 24 696. Thus, for example, the reaction of one mole of pyromellitic acid with 2 moles of 2-phenyl-Δ2-imidazoline in solvents such as dimethyl formamide, dimethyl acetamide, N-methyl pyrrolidone, aliphatic ketones or even alcohols, leads to the disalt of the pyromellitic acid which precipitates owing to its low solubility.

In the same way, the monosalt can be obtained in the above-indicated solvents by a similarly known process by combining pyromellitic acid and 2-phenyl-Δ2-imidaxoline in a mole relationship of 1:1.

Both salts, according to DE-AS No. 23 24 696, are curing agents for epoxy resins for the production of coatings with particularly valuable properties. Thus with the use of the disalt of the pyromellitic acid with 2-phenyl-Δ2-imidazoline as a curing agent for epoxy resins, flat coatings with particularly good mechanical values can be obtained. The monosalt from these components leads to even lower gloss levels though the mechanical properties of the films are thereby diminished so that even relatively slight quantities of monosalt in the disalt are very negatively evident in this respect.

The use of organic solvents in the production of the salts is disadvantageous. Closed apparatus are required both for their production and their processing, toxic and flammable liquids must be processed and the solvents must be purified after the reaction by distillation so as to be able to recycle them. There have, therefore, been experiments seeking to replace the organic solvents with water. The disadvantage here, among others, is the substantially lower solubility of the 2-phenyl-Δ2-imidazoline in water than in the above described solvents. The normal process is to add the pyromellitic acid to the water and, by heating to 70° to 80° C., to obtain a clear solution, after which the stoichiometric quantity of solid 2-phenyl-Δ2-imidazoline corresponding to the mono- or disalt is obtained with stirring. After about 2 hours of stirring at about 90° C. and cooling to room temperature, the precipitated salt is obtained by filtration.

In the examination of technical application of these pyromellitic salts obtained in this way, it was discovered that the least soluble monosalt exhibited values identical with the monosalt precipitated from organic solvents only when employed, as in DE-OS No. 30 26 455, in particle sizes of <60 μm.

In contrast with the monosalt, it was not possible to produce the disalt consistently and optimally from water. The mechanical properties of the coatings produced with epoxy resin according to DE-AS No. 23 24 696 could no longer be attained. A differential thermal analysis of the disalt produced in water indicated that it was contaminated by monosalt.

According to the production mode described above, it is thus not possible to avoid the presence of monosalt in disalt with precipitation from water. It was possible to determine further by experiment that the monosalt, as a result of its low solubility in water, allowed ony incomplete conversion into the disalt, if one mole of 2-phenyl-Δ2-imidazoline were added to the slurry of one mole of monosalt in water. The reaction, even after 12 to 15 hours of boiling of these two components in water, was still not complete and, under these conditions, a partial hydrolytic splitting of the imidazoline ring must be expected.

It was found, surprisingly, that the same good mechanical properties and the same flat gloss degree of hardened epoxy resin layers could be attained if, instead of the disalt of 2-phenyl-Δ2-imidazoline and pyromellitic acid precipitated from organic solvents, a monosalt of 2-phenyl-methyl-Δ2-imidazoline and trimellitic acid was used as a curing agent. In the production of this salt, both organic solvents and water can be employed as a medium without disadvantage. In contrast with the disalt from 2-phenyl-Δ2-imidazoline and pyromellitic acid, the monosalt from 2-phenyl-methyl-Δ2-imidazoline and trimellitic acid is not hygroscopic.

The 2-phenyl-methyl-Δ2-imidazoline can be produced in a known way, for example, by condensation of 1,2-propandiamine with benzonitrile, benzoic acid, or benzoic esters. In the investigation of the substances by nuclear resonance spectroscopy, it was found that what was present was not an isomer mixture but a homogeneous substance. The position of the methyl in the C═N-group, however, cannot be determined. A tautomerism is present:

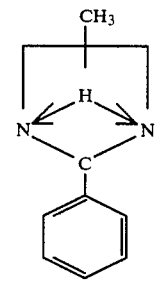

The object of the patent under application is therefore a process for the production of flat varnishes on the basis of powder coatings of 1,2-epoxy compounds with at least one 1,2-epoxy group in the molecule and a lower melting point of >40° C., salts of aromatic carboxylic acids with 3 and more carboxyl groups and imidazolines as curing agents as well as the usual additives and application of the powdered varnish upon the objects to be varnished, whereby these latter are heated to temperatures of 160°–240° C., characterized in that the salt of 2-phenyl-Δ2-imidazoline and trimellitic acid in the mole ratio of 1:1 is used as the accelerator.

As was also further surprisingly found, it is possible, without sacrificing the quality of the flat varnish manufactured in this way, to substitute 2-phenyl-Δ2-imidazoline for 2-phenyl-methyl-Δ2-imidazoline even up to 60 mole %.

EXAMPLES (A) Production of Monosalts (1) Monosalt of trimellitic acid and 2-phenyl-methyl-Δ2-imidazoline (hereinafter referred to as "phenyl-methyl-imidazoline").

0.5 mole of trimellitic acid anhydride is heated in 750 ml of water to about 90° C., whereby hydrolysis and solution occur. At this point, 0.5 mole of phenyl-methyl-imidazoline is metered in at the same temperature. After about 5 minutes the precipitation of the salt begins which is completed by cooling to room temperature. After separation and drying of the fine-cystalline, colorless precipitate, the immediately usable substance is obtained with a yield of 98% of theory.

(2) Monosalt mixtures of trimellitic acid and phenyl-methyl-imidazoline and 2-phenyl-Δ2-imidazoline.

The salt mixtures can be produced appropriately as described under A (1). It is also possible to precipitate the corresponding monosalts separately, to pulverize them and to mix them thoroughly with each other.

(B) Production of the Flat Varnish (1) The monosalt of trimellitic acid and phenyl-methyl-imidazoline was worked up with titanium oxide and the indicated epoxy resin as well as an addition of flow improver in the following relationship to the pulverized varnish:

Solid epoxy resin, on the basis of an adduct of 2,2-bis (4-hydroxy-phenyl)-propane(dian) and epichlorohydrin, which is subjected to an HCl-separation and then reacted with additional dian, and which according to the statement of the manufacturer possesses an epoxy equivalent weight of 900–1000, corresponding to an epoxy value of 0.10–0.11 and a fusion range of 90°–100°: 54.0% by weight Monosalt of trimellitic acid and phenyl-methyl-imidazoline (curing agent): 5.0% by weight
$TiO^2$ (pulverized): 40.0% by weight
Flow improver ("modaflow Powder" ®): 1.0% by weight This formula was applied to the test plates and baked for 10 minutes at 200° C. The subsequent testing produced the following values:

| Coating thickness | 50–60 μm |
| --- | --- |
| Degree of luster (acc. Gardner 60° <) (ASTM D-523-53 T) | 24% |
| Erichsen Cupping Test (DIN 53156) | 6.8 mm |
| Cross Cutting (DIN 53151) | Gt 0 |
| Mandrel test (DIN 53152) | <2 mm |
| Buchholz hardness (DIN 50153) | 111 |
| Ball impact (acc. Gardner) direct impact (ASTM D-2794) | > kg · m |

(2) A mixture of monosalts of trimellitic acids with 2-phenyl-imidazoline and phenyl-methyl imidazoline, in which the two monosalts are present in the mole ratio of 10:90, was used as a curing agent in the formulation of example 1.

After 10 minutes of baking at 200° C. the following technical results with respect to the varnish were obtained:

| Coating thickness | 55–60 μm |
| --- | --- |
| Degree of luster (acc. Gardner 60° <) (ASTM D-523-53 T) | 20% |
| Erichsen cupping test (DIN 53156) | 7.2 mm |
| Cross cutting (DIN 53152) | Gt 0 |
| Mandrel test (DIN 53152) | <2 mm |
| Buchholz hardness (DIN 53153) | 111 |
| Ball impact (acc. Gardner) direct impact (ASTM D2794) | >2 kg · m |

(3) The mixture of monosalts corresponding to example 2, though in the ratio of 20:80, was employed in the formulation of example 1.

After 10 minutes of hardening at 200° the following technical values with respect to the varnish were obtained:

| Coating thickness | 50–60 μm |
| --- | --- |
| Degree of luster (acc. Gardner 60° <) (ASTM D-523-53 T) | 22% |
| Erichsen cupping test (DIN 53156) | 6.8 mm |
| Cross cutting (DIN 53151) | Gt 0 |
| Mandrel test (DIN 53152) | <2 mm |
| Buchholz hardness (DI 53153) | 100 |
| Ball impact (acc. Gardner) Direct impact (ASTM D-2794) | >2 kg · m |

(4) The mixture of the monosalts corresponding to the examples 2 and 3, though in the ratio 30:70, was used as a curing agent in the formulation of example 1.

After 10 minutes at 200° the following test results were obtained.

| Coating thickness | 60–65 μm |
| --- | --- |
| Degree of luster (acc. Gardner 60° <) (ASTM D523-53 T) | 24% |
| Erichsen cupping test (DIN 53156) | 7.3 mm |
| Cross cutting (DIN 5315) | Gt 0 |
| Mandrel test (DIN 53152) | <2 mm |
| Buchholz hardness (DIN 53153) | 111 |
| Ball impact (acc. Gardner) direct impact (ASTM D-2794) | >2 kg · m |

(5) The mixture of monosalts corresponding to the examples 2, 3 and 4, though in the ratio 40:60, was used as an accelerator in the formulation in example 1.

After 15 minutes of baking at 180°, the following technical results with respect to the varnish were obtained.

| Coating thickness | 55–60 μm |
| --- | --- |
| Degree of luster (acc. Gardner 60° <) (ASTM D-523-53T) | 23% |
| Erichsen cupping test (DIN 53156) | 7.8 mm |
| Cross cutting (DIN 53151) | Gt 0 |
| Mandrel test (DIN 53152) | <2 mm |
| Buchholz hardness (DIN 53152) | 100 |
| Ball impact (acc. Gardner) direct impact (ASTM D-2794) | >2 kg · m |

What is claimed as new and desired to be secured by Letters Patent of the United States is:

1. A curing agent for epoxy varnishes, comprising the monosalt reaction product of trimellitic acid and 2-pheny-methyl-Δ2-imidazoline.

2. The curing agent of claim 1, wherein said monosalt is prepared by heating trimellitic acid anhydride in water until hydrolysis occurs, thereafter adding 2-phenyl-methyl-Δ2-imidazoline, said trimellitic acid and 2-phenyl-methyl-Δ2-imidazoline being added in equimolar amounts.

3. The curing agent of claim 1, further comprising a salt reaction product of trimellitic acid and 2-phenyl-Δ2-imidazoline.

4. The curing agent of claim 3, wherein said monosalt is present with said salt reaction product in a molar ratio of at least 4:6.

5. An epoxy varnish comprised of a 1,2-epoxy compound, further comprising a curing agent which is comprised of a monosalt reaction product of trimellitic acid and 2-phenyl-methyl-Δ2-imidazoline.

6. The epoxy varnish of claim 5, wherein said curing agent further compries the salt reaction product of trimellitic acid and 2-phenyl-Δ2-imidazoline, said salt reaction product being present in said curing agent in a molar ratio of up to 6:4.

7. The epoxy varnish of claim 5, said varnish being curable at a temperature 160° C.–240° C.

8. A method of producing a curing agent for epoxy varnishes comprising:
  adding trimellitic acid to water, and heating said suspension until said acid is solublized,
  adding 2-phenyl-methyl-Δ2-imidazoline, and
  recovering the precipitate formed thereby, wherein said trimellitic acid and said 2-phenyl-methyl-Δ2-imidazoline are added in equimolar amounts.

9. The method of claim 8, wherein said suspension is heated to about 90° C.

* * * * *